(12) United States Patent  
Roberts et al.

(10) Patent No.: US 9,449,409 B2
(45) Date of Patent: Sep. 20, 2016

(54) GRAPHICAL INDICATORS IN ANALOG CLOCK FORMAT

(71) Applicants: Timothy Roberts, San Francisco, CA (US); David Wayne Knight, San Francisco, CA (US); Nicholas Adrian Myers, Oakland, CA (US)

(72) Inventors: Timothy Roberts, San Francisco, CA (US); David Wayne Knight, San Francisco, CA (US); Nicholas Adrian Myers, Oakland, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 14/250,590

(22) Filed: Apr. 11, 2014

(65) Prior Publication Data

US 2015/0294487 A1    Oct. 15, 2015

(51) Int. Cl.
*G06T 11/20* (2006.01)
*G04G 9/00* (2006.01)
*G04G 21/00* (2010.01)
*G04G 21/02* (2010.01)

(52) U.S. Cl.
CPC ............... *G06T 11/206* (2013.01); *G04G 9/00* (2013.01); *G04G 21/00* (2013.01); *G04G 21/02* (2013.01); *G04G 21/025* (2013.01)

(58) Field of Classification Search
USPC ........................................................ 345/440
See application file for complete search history.

(56) References Cited

U.S. PATENT DOCUMENTS

| | | |
|---|---|---|
| 2,717,736 A | 9/1955 | Schlesinger |
| 2,883,255 A | 4/1959 | Anderson |
| 3,163,856 A | 12/1964 | Kirby |
| 3,250,270 A | 5/1966 | Bloom |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,575,804 A | 3/1986 | Ratcliff |
| 4,578,769 A | 3/1986 | Frederick |

(Continued)

FOREIGN PATENT DOCUMENTS

| | | |
|---|---|---|
| WO | 2008/038141 A2 | 4/2008 |
| WO | 2009/042965 A1 | 4/2009 |

OTHER PUBLICATIONS

"Forerunner 301 Personal Trainer Owner's Manual", Feb. 2006, Garmin Ltd. or its subsidiaries, Part No. 190-00370-00 Rev. F. 65pgs.

(Continued)

*Primary Examiner* — M Good Johnson
(74) *Attorney, Agent, or Firm* — Buckley, Maschoff & Talwalkar LLC

(57) ABSTRACT

Some aspects relate to display of a plurality of graphical indicators on a display, each of the plurality of graphical indicators associated with a respective time interval, wherein, for each of the plurality of graphical indicators, a length of the displayed graphical indicator represents a value of a metric associated with the respective time interval of the graphical indicator, wherein first ends of each of the plurality of graphical indicators substantially trace an arc of a circle, and wherein, for each graphical indicator, a position of the first end of the graphical indicator on the arc of the circle indicates the respective time interval associated with the graphical indicator.

29 Claims, 13 Drawing Sheets

(56) References Cited

U.S. PATENT DOCUMENTS

| | | | |
|---|---|---|---|
| 4,617,525 A | 10/1986 | Lloyd | |
| 4,887,249 A | 12/1989 | Thinesen | |
| 4,962,469 A * | 10/1990 | Ono et al. | 702/160 |
| 4,977,509 A | 12/1990 | Pitchford et al. | |
| 5,058,427 A | 10/1991 | Brandt | |
| 5,224,059 A | 6/1993 | Nitta et al. | |
| 5,295,085 A | 3/1994 | Hoffacker | |
| 5,323,650 A | 6/1994 | Fullen et al. | |
| 5,446,705 A | 8/1995 | Haas et al. | |
| 5,456,648 A | 10/1995 | Edinburg et al. | |
| 5,583,776 A | 12/1996 | Levi et al. | |
| 5,583,830 A * | 12/1996 | Okuyama | B63C 11/02 368/11 |
| 5,671,162 A | 9/1997 | Werbin | |
| 5,704,350 A | 1/1998 | Williams, III | |
| 5,724,265 A | 3/1998 | Hutchings | |
| 5,737,246 A * | 4/1998 | Furukawa | G04G 21/02 702/166 |
| 5,788,655 A * | 8/1998 | Yoshimura et al. | 600/587 |
| 5,890,128 A | 3/1999 | Diaz et al. | |
| 5,891,042 A | 4/1999 | Sham et al. | |
| 5,894,311 A * | 4/1999 | Jackson | 345/440 |
| 5,899,963 A | 5/1999 | Hutchings | |
| 5,908,396 A * | 6/1999 | Hayakawa et al. | 600/587 |
| 5,947,868 A | 9/1999 | Dugan | |
| 5,955,667 A | 9/1999 | Fyfe | |
| 5,976,083 A | 11/1999 | Richardson et al. | |
| 6,018,705 A | 1/2000 | Gaudet et al. | |
| 6,077,193 A | 6/2000 | Buhler et al. | |
| 6,085,248 A | 7/2000 | Sambamurthy et al. | |
| 6,129,686 A | 10/2000 | Friedman | |
| 6,145,389 A | 11/2000 | Ebeling et al. | |
| 6,183,425 B1 * | 2/2001 | Whalen | A61B 5/1038 600/592 |
| 6,213,872 B1 | 4/2001 | Harada et al. | |
| 6,241,684 B1 | 6/2001 | Amano et al. | |
| 6,269,054 B1 * | 7/2001 | Truini | G04G 9/0082 368/223 |
| 6,287,262 B1 | 9/2001 | Amano et al. | |
| 6,301,964 B1 | 10/2001 | Fyfe et al. | |
| 6,302,789 B2 | 10/2001 | Harada et al. | |
| 6,305,221 B1 | 10/2001 | Hutchings | |
| 6,309,360 B1 | 10/2001 | Mault | |
| 6,469,639 B2 | 10/2002 | Tanenhaus et al. | |
| 6,478,736 B1 | 11/2002 | Mault | |
| 6,513,381 B2 | 2/2003 | Fyfe et al. | |
| 6,513,532 B2 | 2/2003 | Mault et al. | |
| 6,525,997 B1 * | 2/2003 | Narayanaswami et al. | 368/223 |
| 6,527,711 B1 | 3/2003 | Stivoric et al. | |
| 6,529,827 B1 | 3/2003 | Beason et al. | |
| 6,556,222 B1 * | 4/2003 | Narayanaswami | 715/786 |
| 6,561,951 B2 | 5/2003 | Cannon et al. | |
| 6,571,200 B1 | 5/2003 | Mault | |
| 6,583,369 B2 | 6/2003 | Montagnino et al. | |
| 6,585,622 B1 | 7/2003 | Shum et al. | |
| 6,601,988 B2 * | 8/2003 | Molander | G06F 3/04847 368/187 |
| 6,607,493 B2 | 8/2003 | Song | |
| 6,620,078 B2 | 9/2003 | Pfeffer | |
| 6,678,629 B2 | 1/2004 | Tsuji | |
| 6,699,188 B2 | 3/2004 | Wessel | |
| 6,704,016 B1 * | 3/2004 | Oliver | G06F 3/0485 345/440.2 |
| 6,720,860 B1 | 4/2004 | Narayanaswami | |
| 6,761,064 B2 | 7/2004 | Tsuji | |
| 6,790,178 B1 | 9/2004 | Mault et al. | |
| 6,808,473 B2 | 10/2004 | Hisano et al. | |
| 6,811,516 B1 | 11/2004 | Dugan | |
| 6,813,582 B2 | 11/2004 | Levi et al. | |
| 6,813,931 B2 | 11/2004 | Yadav et al. | |
| 6,856,938 B2 | 2/2005 | Kurtz | |
| 7,035,170 B2 * | 4/2006 | Narayanaswami et al. | 368/223 |
| 7,062,225 B2 | 6/2006 | White | |
| 7,113,450 B2 * | 9/2006 | Plancon | G04B 19/082 368/10 |
| 7,162,368 B2 | 1/2007 | Levi et al. | |
| 7,167,743 B2 * | 1/2007 | Heruth et al. | 600/509 |
| 7,171,331 B2 | 1/2007 | Vock et al. | |
| 7,200,517 B2 | 4/2007 | Darley et al. | |
| 7,246,033 B1 | 7/2007 | Kudo | |
| 7,261,690 B2 | 8/2007 | Teller et al. | |
| 7,272,982 B2 | 9/2007 | Neuhauser et al. | |
| 7,278,966 B2 * | 10/2007 | Hjelt et al. | 600/300 |
| 7,373,820 B1 | 5/2008 | James | |
| 7,443,292 B2 | 10/2008 | Jensen et al. | |
| 7,457,724 B2 | 11/2008 | Vock et al. | |
| 7,467,060 B2 | 12/2008 | Kulach et al. | |
| 7,505,865 B2 | 3/2009 | Ohkubo et al. | |
| 7,533,326 B2 | 5/2009 | Chambers | |
| 7,559,877 B2 | 7/2009 | Parks et al. | |
| 7,623,415 B2 * | 11/2009 | Raeber | B63C 11/32 368/10 |
| 7,653,508 B1 | 1/2010 | Kahn et al. | |
| 7,690,556 B1 | 4/2010 | Kahn et al. | |
| 7,713,173 B2 | 5/2010 | Shin et al. | |
| 7,717,866 B2 * | 5/2010 | Damen | 600/595 |
| 7,738,320 B2 * | 6/2010 | Taha | G01D 7/02 345/440 |
| 7,774,156 B2 | 8/2010 | Niva et al. | |
| 7,789,802 B2 | 9/2010 | Lee et al. | |
| 7,881,802 B2 | 2/2011 | Quiles et al. | |
| 7,927,253 B2 | 4/2011 | Vincent et al. | |
| 7,940,604 B2 * | 5/2011 | Inoue | B60K 37/02 368/223 |
| 7,959,539 B2 * | 6/2011 | Takeishi et al. | 482/8 |
| 7,983,876 B2 | 7/2011 | Vock et al. | |
| 8,028,443 B2 | 10/2011 | Case, Jr. | |
| 8,055,469 B2 | 11/2011 | Kulach et al. | |
| 8,099,318 B2 | 1/2012 | Moukas et al. | |
| 8,177,260 B2 | 5/2012 | Tropper et al. | |
| 8,180,591 B2 | 5/2012 | Yuen et al. | |
| 8,180,592 B2 | 5/2012 | Yuen et al. | |
| 8,311,769 B2 | 11/2012 | Yuen et al. | |
| 8,311,770 B2 | 11/2012 | Yuen et al. | |
| 8,350,856 B1 * | 1/2013 | Nazir et al. | 345/440 |
| 8,386,008 B2 | 2/2013 | Yuen et al. | |
| 8,437,980 B2 | 5/2013 | Yuen et al. | |
| 8,463,576 B2 | 6/2013 | Yuen et al. | |
| 8,463,577 B2 | 6/2013 | Yuen et al. | |
| 8,475,367 B1 | 7/2013 | Yuen et al. | |
| 8,543,185 B2 | 9/2013 | Yuen et al. | |
| 8,543,351 B2 | 9/2013 | Yuen et al. | |
| 8,548,770 B2 | 10/2013 | Yuen et al. | |
| 8,583,402 B2 | 11/2013 | Yuen et al. | |
| 8,597,093 B2 | 12/2013 | Engelberg et al. | |
| 8,615,377 B1 | 12/2013 | Yuen et al. | |
| 8,620,617 B2 | 12/2013 | Yuen et al. | |
| 8,670,953 B2 | 3/2014 | Yuen et al. | |
| 2001/0055242 A1 | 12/2001 | Deshmukh et al. | |
| 2002/0013717 A1 | 1/2002 | Ando et al. | |
| 2002/0077219 A1 | 6/2002 | Cohen et al. | |
| 2002/0082144 A1 | 6/2002 | Pfeffer | |
| 2002/0109600 A1 | 8/2002 | Mault et al. | |
| 2002/0178060 A1 | 11/2002 | Sheehan | |
| 2002/0198776 A1 | 12/2002 | Nara et al. | |
| 2003/0018523 A1 | 1/2003 | Rappaport et al. | |
| 2003/0050537 A1 | 3/2003 | Wessel | |
| 2003/0065561 A1 | 4/2003 | Brown et al. | |
| 2003/0131059 A1 | 7/2003 | Brown et al. | |
| 2004/0054497 A1 | 3/2004 | Kurtz | |
| 2004/0061324 A1 | 4/2004 | Howard | |
| 2004/0117963 A1 | 6/2004 | Schneider | |
| 2004/0152957 A1 | 8/2004 | Stivoric et al. | |
| 2005/0037844 A1 | 2/2005 | Shum et al. | |
| 2005/0038679 A1 | 2/2005 | Short | |
| 2005/0054938 A1 | 3/2005 | Wehman et al. | |
| 2005/0102072 A1 | 5/2005 | Deakin | |
| 2005/0102172 A1 | 5/2005 | Sirmans, Jr. | |
| 2005/0107723 A1 | 5/2005 | Wehman et al. | |
| 2005/0202934 A1 * | 9/2005 | Olrik et al. | 482/8 |
| 2005/0228692 A1 | 10/2005 | Hodgdon | |
| 2005/0234742 A1 | 10/2005 | Hodgdon | |
| 2005/0248718 A1 | 11/2005 | Howell et al. | |
| 2005/0272564 A1 | 12/2005 | Pyles et al. | |

(56) References Cited

U.S. PATENT DOCUMENTS

| | | |
|---|---|---|
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0129436 A1 | 6/2006 | Short |
| 2006/0143645 A1 | 6/2006 | Vock et al. |
| 2006/0264730 A1* | 11/2006 | Stivoric et al. ............... 600/390 |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0208544 A1 | 9/2007 | Kulach et al. |
| 2007/0276271 A1 | 11/2007 | Chan |
| 2008/0062819 A1* | 3/2008 | Kelly et al. ..................... 368/11 |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2008/0249836 A1 | 10/2008 | Angell et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063293 A1 | 3/2009 | Mirrashidi et al. |
| 2009/0171788 A1 | 7/2009 | Tropper et al. |
| 2009/0271147 A1 | 10/2009 | Sugai |
| 2010/0331145 A1 | 12/2010 | Lakovic et al. |
| 2010/0331657 A1 | 12/2010 | Mensinger et al. |
| 2011/0003665 A1 | 1/2011 | Burton et al. |
| 2011/0009051 A1 | 1/2011 | Khedouri et al. |
| 2011/0009727 A1 | 1/2011 | Mensinger et al. |
| 2011/0022349 A1 | 1/2011 | Stirling et al. |
| 2011/0032105 A1 | 2/2011 | Hoffman et al. |
| 2011/0080349 A1 | 4/2011 | Holbein et al. |
| 2011/0106449 A1 | 5/2011 | Chowdhary et al. |
| 2011/0126143 A1* | 5/2011 | Williams et al. ............. 715/771 |
| 2011/0131005 A1 | 6/2011 | Ueshima et al. |
| 2011/0193704 A1 | 8/2011 | Harper et al. |
| 2012/0020649 A1* | 1/2012 | Vanderkaden ................ 386/280 |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265326 A1* | 10/2012 | Prstojevich et al. ............ 700/91 |
| 2012/0265480 A1 | 10/2012 | Oshima |
| 2012/0274508 A1 | 11/2012 | Brown et al. |
| 2012/0316471 A1 | 12/2012 | Rahman et al. |
| 2012/0330109 A1 | 12/2012 | Tran |
| 2013/0006718 A1 | 1/2013 | Nielsen et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0163390 A1 | 6/2013 | Gossweiler, III et al. |
| 2013/0231574 A1 | 9/2013 | Tran |
| 2013/0267249 A1 | 10/2013 | Rosenberg |
| 2013/0268236 A1 | 10/2013 | Yuen et al. |
| 2013/0280682 A1 | 10/2013 | Levine et al. |
| 2013/0310896 A1 | 11/2013 | Mass |
| 2013/0325396 A1* | 12/2013 | Yuen et al. ................... 702/160 |
| 2013/0325399 A1 | 12/2013 | Yuen et al. |
| 2014/0035761 A1 | 2/2014 | Burton et al. |
| 2014/0039804 A1 | 2/2014 | Park et al. |
| 2014/0039839 A1 | 2/2014 | Yuen et al. |
| 2014/0039840 A1 | 2/2014 | Yuen et al. |
| 2014/0039841 A1 | 2/2014 | Yuen et al. |
| 2014/0039842 A1 | 2/2014 | Yuen et al. |
| 2014/0052790 A1 | 2/2014 | Yuen et al. |
| 2014/0067278 A1 | 3/2014 | Yuen et al. |
| 2014/0107493 A1 | 4/2014 | Yuen et al. |
| 2014/0125491 A1 | 5/2014 | Park et al. |
| 2014/0127996 A1 | 5/2014 | Park et al. |
| 2014/0129243 A1* | 5/2014 | Utter, II ............................ 705/2 |
| 2014/0135631 A1 | 5/2014 | Brumback et al. |
| 2014/0142403 A1 | 5/2014 | Brumback et al. |

OTHER PUBLICATIONS

"Quick Installation Guide", Withings Pulse, Jul. 24, 2013, 16pgs. withings.com/pulse.

Cooper, Daniel, "Withings Pulse review", Aug. 16, 2013, http://www.engadget.com/2013/08/16/withings-pulse-review/, (pp. 1-8, total 8 pages).

Desmarais, Christina, "Which New Activity Tracker is Best for You?", Sep. 3, 2013, retrieved Sep. 23, 2013, retrieved from http://www.techlicious.com/guide/which-new-activity-tracker-is-right-for-you/, (pp. 1-4, total 4 pages).

Lester, Jonathan et al., "Validated Caloric Expenditure Estimation using a Single Body-Worn Sensor", UbiComp 2009, Sep. 30-Oct. 3, 2009, Orlando, Florida, USA, ACM 978-1-60558-431-7/09/09 (pp. 225-234, total 10 pages).

Intersema, "Using MS5534 for altimeters and barometers", AN501. doc, Application Note, www.intersema.ch, (pp. 1-12, total 12 pages).

Suunto Lumi "User Guide" Jun. 2007, Sep. 2007, 49 pages.

VTI Technologies Oy, "SCP100-D01/D11 Pressure Sensor as Barometer and Altimeter", Application Note 33, www.vti.fi, 3pgs.

"Forerunner 405 Owner's Manual: GPS-Enabled Sports Watch With Wireless Sync", Mar. 2011, Garmin Ltd. or its subsidiaries, Part No. 190-00700-00 Rev. D, 54pgs.

"Forerunner 410 Owner's Manual: GPS-Enabled Sports Watch With Wireless Sync", Jul. 2012, Garmin Ltd. or its subsidiaries, Part No. 190-01274-00 Rev. B, 50pgs.

"Forerunner 405CX Owner's Manual: GPS-Enabled Sports Watch With Wireless Sync", Mar. 2009, Garmin Ltd. or its subsidiaries, Part No. 190-01066-00 Rev. B, 55pgs.

"Forerunner 310XT Owner's Manual: Multisport GPS Training Device", 2009, Garmin Ltd. or its subsidiaries, Part No. 190-01066-00 Rev. B, 56pgs.

Ohtaki, Yasuaki et al., "Automatic classification of ambulatory movements and evaluation of energy consumptions utilizing accelerometers and a barometer", Microsyst Technol (2005) 11, DOI: 10.1007/s00542-005-0502-z, (pp. 1034-1040, total 7 pages).

Retscher, G. "An Intelligent Multi-sensor System for Pedestrian Navigation", Journal of Global Positioning Systems, (2006), vol. 5, No. 1-2, (pp. 110-118, 9 total pages).

Clifford, Michelle et al., "Altimeter and Barometer System", Freescale Semiconductor Application Note, AN1979, Rev. 3, Nov. 2006, 10pgs.

Parkka, Juha et al., "Activity Classification Using Realistic Data From Wearable Sensors", IEEE Transactions on Information Technology in Biomedicine, vol. 10, No. 1, Jan. 2006, (pp. 119-128, total 10 pages).

DC Rainmaker, "Basis Bi Watch In-Depth Review", Feb. 4, 2014, http://www.dcrainmaker.com/2013/07/basis-bi-review.html, 56pgs.

Lester, Jonathan et al., "A Hybrid Discriminative/Generative Approach for Modeling Human Activities", IJCAI'05 Proceedings of the 19th International Joint Conference on Artificial Intelligence, 2005, 7pgs.

(56) References Cited

OTHER PUBLICATIONS

"Activator is One of the Best Cydia iPhone Hacks", retrieved on Jul. 9, 2013, download from http://www.iphone-tips-and-advice.com/activator.html, 10pgs.

"Forerunner 50 Owner's Manual: With ANT+Sport wireless technology", Nov. 2007, Garmin Ltd. or its subsidiaries, Part No. 190-00839-00 Rev. E, 44pgs.

"Forerunner 10 Owner's Manual", Aug. 2012, Garmin Ltd. or its subsidiaries, Part No. 190-01472-00_OA, 8pgs.

"Forerunner 110 Owner's Manual: GPS-Enabled Sports Watch", Dec. 2010, Garmin Ltd. or its subsidiaries, Part No. 190-01154-00 Rev. D, 16pgs.

"Forerunner 201 Personal Trainer Owner's Manual", Feb. 2006, Garmin Ltd. or its subsidiaries, Part No. 190-00318-00 Rev. F, 48pgs.

"Forerunner 210 Owner's Manual: GPS-Enabled Sports Watch", Dec. 2010, Garmin Ltd. or its subsidiaries, Part No. 190-01273-00 Rev. B, 28pgs.

* cited by examiner

GRAPHICAL INDICATORS IN ANALOG CLOCK FORMAT

BACKGROUND

1. Field

The embodiments described below relate to the generation and presentation of time-related data. Some embodiments relate to the display of a graphical indicator to represent a value of a metric and a time interval associated with the value.

2. Description

Modern computing systems collect large amounts of data. The collected data may be processed in order to generate even more data. A user's ability to determine facts and trends based on such data is often hampered by the volume and complexity of the data.

Visualizations (e.g., charts, graphs, etc.) may be used to present data to users. Typically, the goal of a visualization is to convey data to users in an easy-to-understand format. Time-related data presents special considerations. For example, a visualization of time-related data should efficiently convey both data and associated time periods. These concerns are exacerbated for visualizations presented on small display screens, which are increasingly common.

Systems are desired for efficiently presenting time-related data.

SUMMARY

Some embodiments relate to a device, method, and/or computer-readable medium storing processor-executable process steps to display a plurality of graphical indicators on a display, each of the plurality of graphical indicators associated with a respective time interval, wherein, for each of the plurality of graphical indicators, a length of the displayed graphical indicator represents a value of a metric associated with the respective time interval of the graphical indicator, wherein first ends of each of the plurality of graphical indicators substantially trace an arc of a circle, and wherein, for each graphical indicator, a position of the first end of the graphical indicator on the arc of the circle indicates the respective time interval associated with the graphical indicator.

In some aspects, the value of the metric associated with a respective time interval is indicative of physical activity during the respective time interval. For example, the metric may be step count, heart rate, distance traveled, activity level, altitude ascended, altitude descended, floors climbed, or calories burned.

According to some aspects, arcs of the circle represent a plurality of time intervals totaling one hour, but other time intervals may be represented (e.g., twelve hours, twenty-four hours). Moreover, the angular distance of the arc of the circle may indicate the current time.

A current time may be displayed within the circle. In some aspects, displayed within the circle may be a current value of a step count, a current value of a heart rate, a current value of a distance traveled, a current value of an activity level, a current value of an altitude increase, a current value of floors gained, or a current value of calories burned.

In some aspects, one of the plurality of graphical indicators associated with a respective time interval comprises M graphical icons, and M represents a value of the metric associated with the respective time interval.

According to some aspects, a plurality of graphical indicators are displayed on a display, each of the plurality of graphical indicators comprising a respective number of graphical icons and associated with a respective time interval, wherein first ends of each of the plurality of graphical indicators substantially trace an arc of a circle. For each graphical indicator, the respective number of graphical icons of the graphical indicator represents a value of a metric associated with the respective time interval of the graphical indicator, the value of the metric being indicative of physical activity during the respective time interval, and, for each graphical indicator, a position of the first end of the graphical indicator along the arc of the circle indicates the respective time interval associated with the one of the plurality of graphical indicators.

Further aspects include detection of a signal indicative of physical activity, and determination of the value of the metric associated with a respective time interval based on the signal. In some aspects, a current time is displayed within the circle, wherein the angular distance of the arc of the circle indicates the current time. One of the plurality of graphical indicators associated with a respective time interval may include M graphical icons, wherein M represents a value of the metric associated with the respective time interval.

According to some aspects, a plurality of graphical indicators are determined, each of the plurality of graphical indicators associated with a respective time interval; and data representing the plurality of graphical indicators is transmitted to a device comprising a display screen. For each of the plurality of graphical indicators, a length of the displayed graphical indicator represents a value of a metric associated with the respective time interval of the graphical indicator. First ends of each of the plurality of graphical indicators substantially trace an arc of a circle, and, for each graphical indicator, a position of the first end of the graphical indicator on the arc of the circle indicates the respective time interval associated with the graphical indicator.

A more complete understanding of some embodiments can be obtained by referring to the following detailed description and to the drawings appended hereto.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments. Various modifications, however, will remain readily apparent to those in the art.

A specific example will now be described with reference to FIG. 1 in order to provide an introduction to various features. Embodiments are not limited to the features or description of this example.

Figure 1:
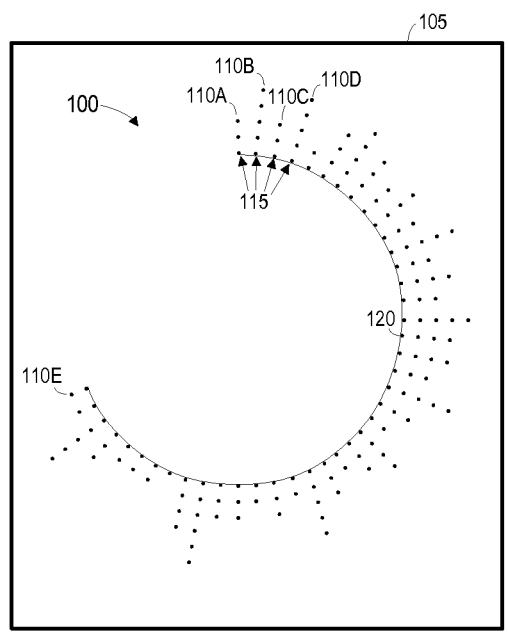
FIG. 1 is an outward view of displayed graphical indicators according to some embodiments.

FIG. 1 is an outward view of visualization 100 displayed on display 105 according to some embodiments. A specific example will now be described with reference to visualization 100 in order to provide an introduction to various features. Embodiments are not limited to the features or description of this example.

According to the example, visualization 100 includes several graphical indicators (e.g., 110A, 110B, 110C, 110D and 110E). The length of a graphical indicator represents a heart rate over a time interval. For example, each dot of a graphical indicator represents 30 beats per minute (BPM). Therefore, indicator 110A, which includes three dots, represents 90 BPM.

The position of the graphical indicator indicates the time interval associated with the graphical indicator. Continuing the present example, graphical indicator 110A is positioned at the '0' minute position of a traditional analog clock layout, therefore graphical indicator 110A is associated with the 60th minute of the prior hour. More specifically, graphical indicator 110a indicates a heart rate of 90 BPM over the 60th minute of the prior hour.

Similarly, graphical indicator 110B indicates a heart rate of 150 BPM over the first minute of the current hour, graphical indicator 110C indicates a heart rate of 90 BPM over the second minute of the current hour, graphical indicator 110D indicates a heart rate of 150 BPM over the third minute of the current hour, and graphical indicator 110E indicates a heart rate of 60 BPM over the forty-first minute of the current hour. Accordingly, some embodiments efficiently convey values associated with respective time intervals in an intuitive manner which can be quickly grasped by a user.

More generally, embodiments are not limited to the graphical indicators of FIG. 1. Each of the plurality of graphical indicators represents a value of a metric. The metric may comprise any metric that is or become known. According to some embodiments, the metric is one of step count, heart rate, distance traveled, activity level, altitude changes, altitude ascended, altitude descended, floors climbed, and calories burned. The metric may be indicative of physical activity, but embodiments are not limited thereto.

In the present disclosure, the term "activity" includes sedentary and nonsedentary activities. As such, the metric may be associated with activities related to sleeping, lying, sitting, and standing stationary (for example, time asleep, the onset, duration, and number of awakenings while attempting to sleep, the time spent in various stages of sleep, sleep latency, sleep efficiency and other sleep quality parameters, the presence of sleep apnea and other diagnostic measures, time spent in a prone non-standing state, and resting heart rate).

A length of a displayed graphical indicator represents a value of the metric. For example, a longer graphical indicator may represent a higher heart rate than a shorter graphical indicator. According to a more specific example, a length of a graphical indicator may conform to a predetermined ratio of length/metric value (e.g., 0.1 inch/10 beats per minute). Any suitable ratio may be implemented in some embodiments, and may be dependent upon a size of display 105.

Each of the plurality of graphical indicators of FIG. 1 includes a number of graphical icons, but embodiments are not limited thereto. The graphical icons of visualization 100 comprise dots, but one or more other icons may be used. Each graphical icon represents a value of the metric associated with the graphical indicator. For example, each graphical icon may represent 10 steps, such that graphical indicator 110A, which includes three dots, represents a step count of 30.

According to some embodiments, the graphical icons of a graphical indicator may exhibit different colors. Different colors may represent different values of a metric. For example, a blue icon may represent 30 BPM and a red icon may represent 1 BPM. Accordingly, a graphical indicator consisting of two blue icons and three red icons may represent a value of sixty-three BPM.

Each of the plurality of graphical indicators represents a value of a metric and a time interval. The time interval associated with a graphical indicator is indicated by a position of the graphical indicator. More specifically, the ends of each graphical indicator substantially trace an arc of a circle, numbered 120 in FIG. 1. Arc 120 may or may not be displayed according to some embodiments. The position of an end of a graphical indicator on arc 120 indicates the time interval associated with the graphical indicator.

Distal ends 115 of graphical indicators 110A through 110D are located on arc 120 at the :00, :01, :02 and :03 positions of an analog clock, respectively. As described in the above example, these positions correspond to time intervals which are one minute in length. The time intervals associated with each graphical indicator may exhibit any duration. For example, each position of an end 115 may correspond to a five minute interval, a ten minute interval, or an interval of any duration. In a case that a complete circle includes sixty graphical indicators and corresponds to twelve hours, each graphical indicator is associated with a twelve minute interval. Similarly, in a case that a complete circle includes sixty graphical indicators and corresponds to twenty-four hours, each graphical indicator is associated with a twenty-four minute interval.

Figure 2:
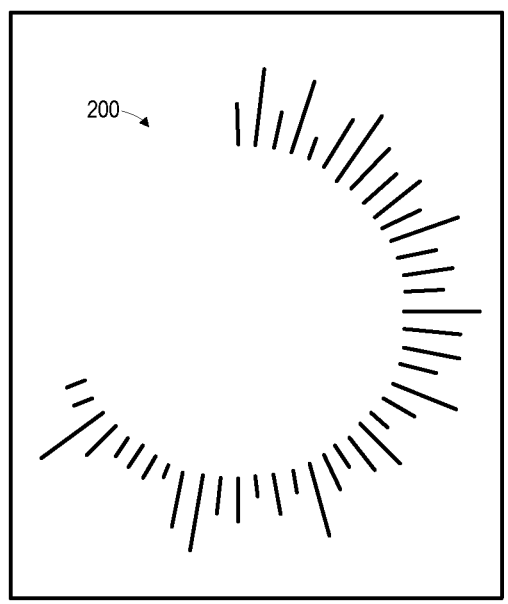
FIG. 2 is an outward view of displayed graphical indicators according to some embodiments.

FIG. 2 is an outward view of visualization 200 according to some embodiments. Visualization 200 is identical to visualization 100 excepting that each graphical indicator of visualization 200 is a solid, as opposed to a dotted, line. Again, the length of a graphical indicator of visualization 200 represents a value of a metric over a time interval, the ends of each of the graphical indicators substantially trace an arc of a circle, and a position of an end of a graphical indicator on the arc of the circle indicates the time interval associated with the graphical indicator.

Embodiments are not limited to the graphical indicators described above and/or illustrated in FIGS. 1 and 2. A visualization according to some embodiments may include two or more types of graphical indicators. A visualization according to some embodiments may include additional elements, examples of which will be provided below.

Figure 3:
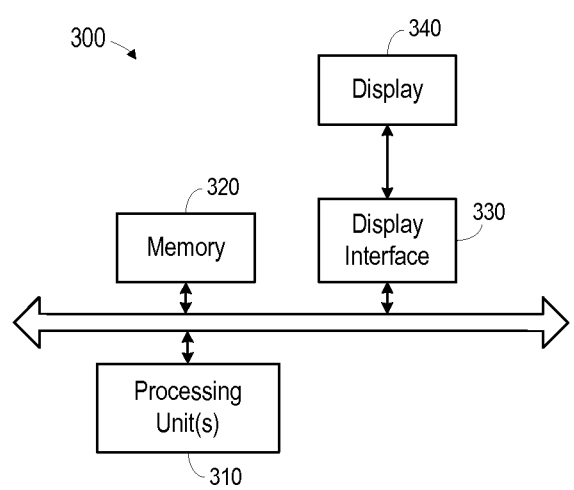
FIG. 3 is a block diagram of a device according to some embodiments.

FIG. 3 is a block diagram of system 300 according to some embodiments. System 300 may be operated to generate and/or display a visualization according to some embodiments. System 300 includes one or more processing units 310 (e.g., processor cores and/or processing threads, discrete or integrated logic, and/or one or more state machines, and/or field programmable gate arrays (or combinations thereof)). One or more processing units 310 are configured to execute processor-executable program code to cause system 300 to operate as described herein, and memory 320 for storing the program code and any other suitable data, including but not limited to values of metrics associated with respective time intervals. Memory 320 may comprise one or more fixed disks, solid-state random access memory, and/or removable media (e.g., a thumb drive) mounted in a corresponding interface (e.g., a USB port).

Display interface 330 provides communication with display 340, which may comprise any system for visual presentation of information that is or becomes known. Display 340 may comprise a touch screen for receiving user input into system 300 according to some embodiments.

One or more processing units 310 may therefore execute processor-executable program code stored in memory 320 to cause system 300 to determine a plurality of graphical indicators associated with respective time intervals, wherein a length of each graphical indicator represents a value of a metric associated with the respective time interval of the graphical indicator, and to display the plurality of graphical indicators on display 340, wherein first ends of each of the plurality of graphical indicators substantially trace an arc of a circle, and wherein, for each graphical indicator, a position of the first end of the graphical indicator on the arc of the circle indicates the respective time interval associated with the graphical indicator.

According to some embodiments, system 300 comprises an integrated device such as, but not limited to, a wearable unit (e.g., around wrist, around neck) or an otherwise portable unit (e.g., a smartphone, a dedicated music player, a fob). In some embodiments, elements of system 300 may be embodied in separate devices, such as a server device (e.g., a desktop computer) including elements 310, 320 and 330, and a terminal device (e.g., a watch) including display 340. System 300 may perform functions other than those attributed thereto herein, and may include any elements which are necessary for the operation thereof.

Some embodiments of system 300 include a portable monitoring device having a physical size and shape adapted to couple to the body of a user, which allows the user to perform normal or typical user activities (including, for example, exercise of all kinds and type) without hindering the user from performing such activities. The portable monitoring device may include a mechanism (for example, a clip, strap and/or tie) that facilitates coupling or affixing the device to the user during such normal or typical user activities.

For example. during operation, an altitude sensor generates data which is representative of the altitude and/or changes in altitude of the user. A motion sensor generates data which is representative of motion of the user. The data which is representative of the altitude and/or changes in altitude and the data which is representative of the motion of the user, is used to determine energy and/or calorie "burn" of the user.

The data may also be used to determine other activity-related metrics including, for example, (i) in the context of running/walking on level, substantially level, or relatively level ground, (a) number of steps, which may be categorized according to the number of steps associated with a user state, for example, walking, jogging and/or running, (b) distance traveled and/or (c) pace, (ii) in the context of running/jogging/walking/jumping on stairs, hills or ground having a grade of greater than, for example, about 3%, (a) number of stair and/or hill steps, which may be categorized, correlated or organized/arranged according to the number of stair and/or hill steps pertaining to, for example, the speed, pace and/or user state of the user (for example, walking, jogging and/or running), (b) number of flights of stairs, (c) ascent/descent distance on stairs and/or hills, (d) pace, (e) ascent/descent on elevators and/or escalators, (f) number of calories burned or expended by walking/running on stairs and/or hills and/or (g) quantify/compare the additional calories expended or burnt from stairs/hills relative to, versus or over level ground, (iii) in the context of swimming, number of strokes, time between strokes, leg kicks and similar metrics (variance of stroke time, mean stroke time, etc.), depth underwater, strokes per lap, lap time, pace and/or distance, (iv) in the context of using a bicycle, wheelchair, skateboard, skis, snowboard, ladder, etc., (a) ascent/descent distance traversed, (b) number of additional calories expended, (c) time of a downward "run" or upward "climb", (d) number of calories expended, (e) number of pedal rotations, (f) arm or wheel rotation, (g) the grade of the surface, (h) pushes, kicks and/or steps. This list of activities (if applicable to the particular embodiment) is merely exemplary and is not intended to be exhaustive or limiting.

Figure 4:
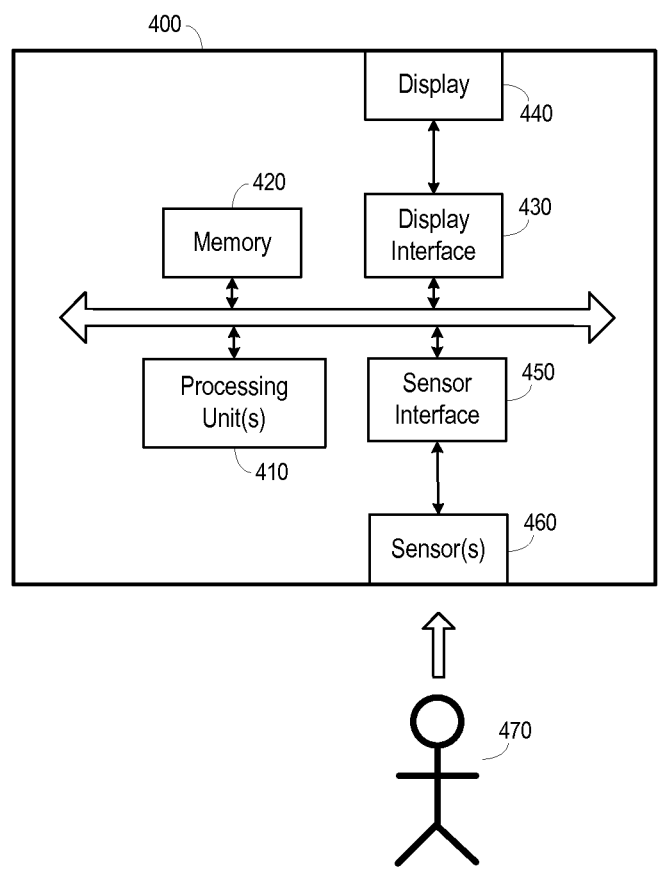
FIG. 4 is a block diagram of a device according to some embodiments.

FIG. 4 is a block diagram of device 400 according to some embodiments. Device 400 may comprise an implementation of system 300 of FIG. 3. Device 400 incorporates elements 410 through 460 into a single integrated package.

Elements 410 through 440 of device 400 may operate as described above with respect to similarly-numbered elements of system 300. Device 400 further includes sensor interface 450 for exchanging data with one or more sensors 460.

Sensors 460 may comprise any sensors for acquiring data based on which metric values may be determined. Examples of sensors 460 include, but are not limited to, an accelerometer, a light sensor, a compass, a switch, a pedometer, a blood oxygen sensor, a gyroscope, a magnetometer, a Global Positioning System device, a proximity sensor, an altimeter, and a heart rate sensor. One or more of sensors 460 may share common hardware and/or software components.

A value of a metric may be determined based on data acquired by one or more of sensors 460. For example, a value of a "distance traveled" metric may be determined based on the outputs of a Global Positioning System device and an altimeter. An "activity level" metric may be determined based on the outputs of a blood oxygen sensor and a heart rate sensor.

User 470 is pictured to indicate that, according to some embodiments, user 470 influences the data acquired by one or more of the one or more sensors 460. For example, the one or more sensors 460 may generate data based on physical activity of user 470. Moreover, one or more of sensors 460 may generate data via direct contact with the user, for example during heart rate, skin temperature, and/or blood oxygen monitoring.

In some embodiments, calorie expenditure and activity level may be determined based on or using, partially or entirely, the ambulatory speed of user 470. The speed of the user may be calculated, determined and/or estimated as the user's step count over a time epoch multiplied by one or more step lengths of the user (which may be programmed, predetermined and/or estimated (for example, based on attributes of the user (for example, height, weight, age, leg length, and/or gender))). Representative energy expenditure rates expressed as metabolic equivalents per minute (MET/min) may then be estimated, obtained (for example, from a look-up table or database) and/or interpolated from a MET table which provides metabolic equivalents per minute for different user speeds. In some embodiments, step length may be one of two values that are indicative of a walking step length and a running step length dependent on the step frequency and/or acceleration characteristics of the user. In some embodiments, step length may be described as a linear function of step frequency: step length=A+B*step frequency, where A and B are parameters that may be associated with or calibrated to the user. Such parameters may be stored in memory in device 400.

In some embodiments, the speed value may be converted to calorie expenditure by multiplying the corresponding MET value by the user's Body Mass Ratio (BMR). BMR may be obtained through any of a number of well-known equations based on height, weight, gender, age, and/or athletic ability or through designated BMR measurement devices. For example, a user may have a running step length of 57 inches and take 180 running steps during 1 min. Using the method described above, the user's speed estimate is 9.8 miles per hour, which may be linearly interpolated to provide a BMR value of 15.8 MET from the MET table above. Assuming the user's BMR to be 1.10 kcal/MET, the calorie burn of the user in the preceding minute is 17.4 kcal.

An intermediate MET calculation step is not required in this and similar methods. Calorie expenditure may be calculated directly based on speed and one or more physiological parameters of the user such as age, gender, height, weight, and/or athletic ability. Speed may also be filtered over time rather than accepted as a "raw" measurement for a given time epoch. All forms of speed estimation, and mechanisms to implement such techniques, whether now known and/or later developed, may be implemented in some embodiments Calorie consumption, burn and/or expenditure may be determined using data which is representative of the intensity of user motion for example, as provided or determined by one or more single axis or multi-axis accelerometers, based on a heart rate, based on altitude-related information (for example, from an altimeter disposed on the portable monitoring device), and/or based on any combination of factors described herein.

Figure 5:
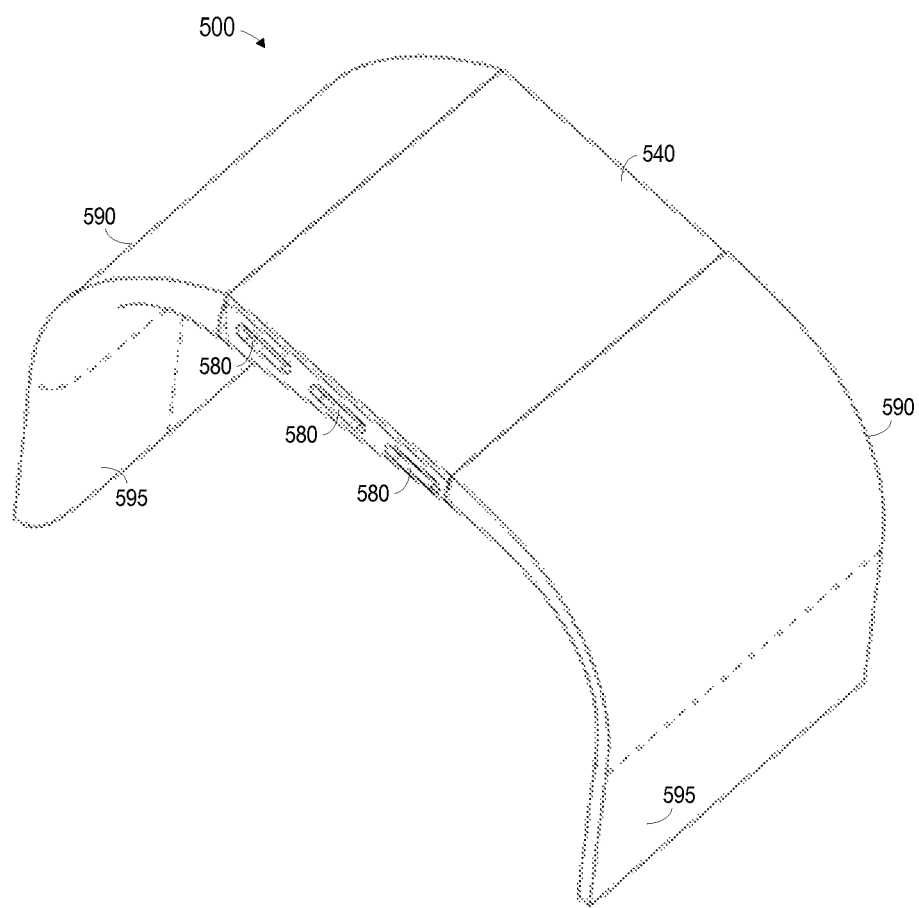
FIG. 5 is a top perspective view of a device according to some embodiments.

FIG. 5 is a top view of one implementation of device 400 according to some embodiments. According to the illustrated embodiment, device 500 is wearable on a user's wrist. Device 500 includes display 540, which may comprise any suitable type of display screen, and which may display graphical indicators as described herein. Buttons 580 may be manipulated by a user to provide input to device 500. As described above, display 540 may also incorporate an input device (i.e., a touch screen). Band 590 may be wrapped around the wrist and is securable using securing elements 595 (e.g., hook and loop, clasp, shape memory elements).

Figure 6:
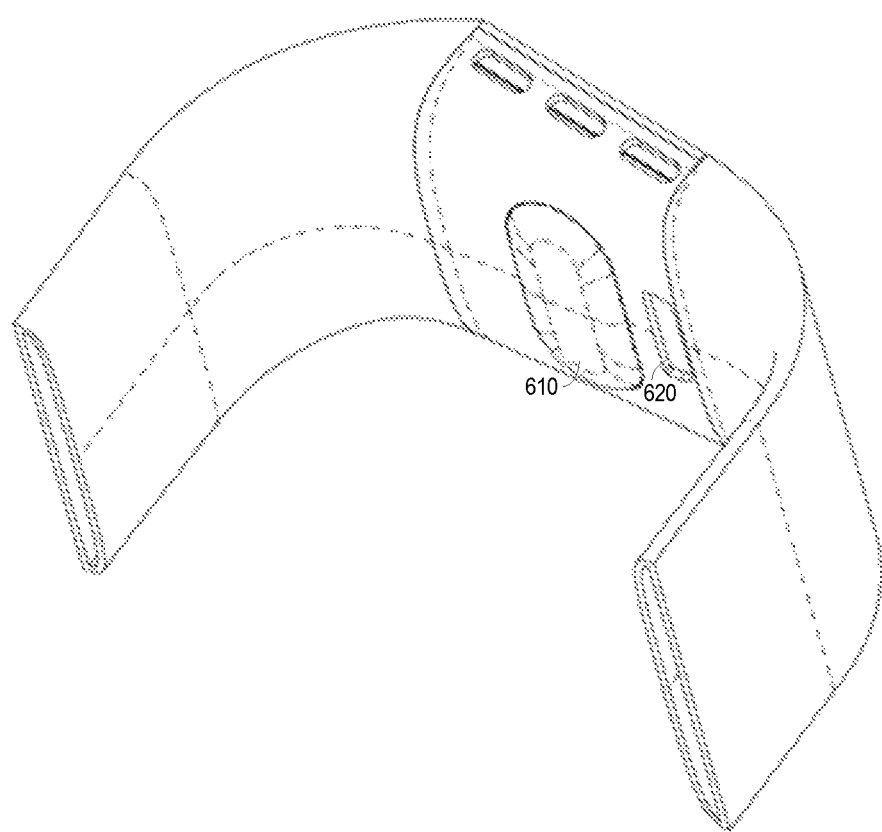
FIG. 6 is a bottom perspective view of a device according to some embodiments.

FIG. 6 is a bottom view of device 500, showing sensor protrusion 610 and power interface 620. Sensor protrusion 610 may include sensors which benefit from close proximity and/or contact with a user's skin. Such sensors may include heart rate, moisture and/or temperature sensors. Power interface 620 may interface with a docking station or other power source to receive electrical charge for charging of batteries located within device 500. Embodiments are not limited to device 500 in terms of function, features and/or form factor.

Figure 7:
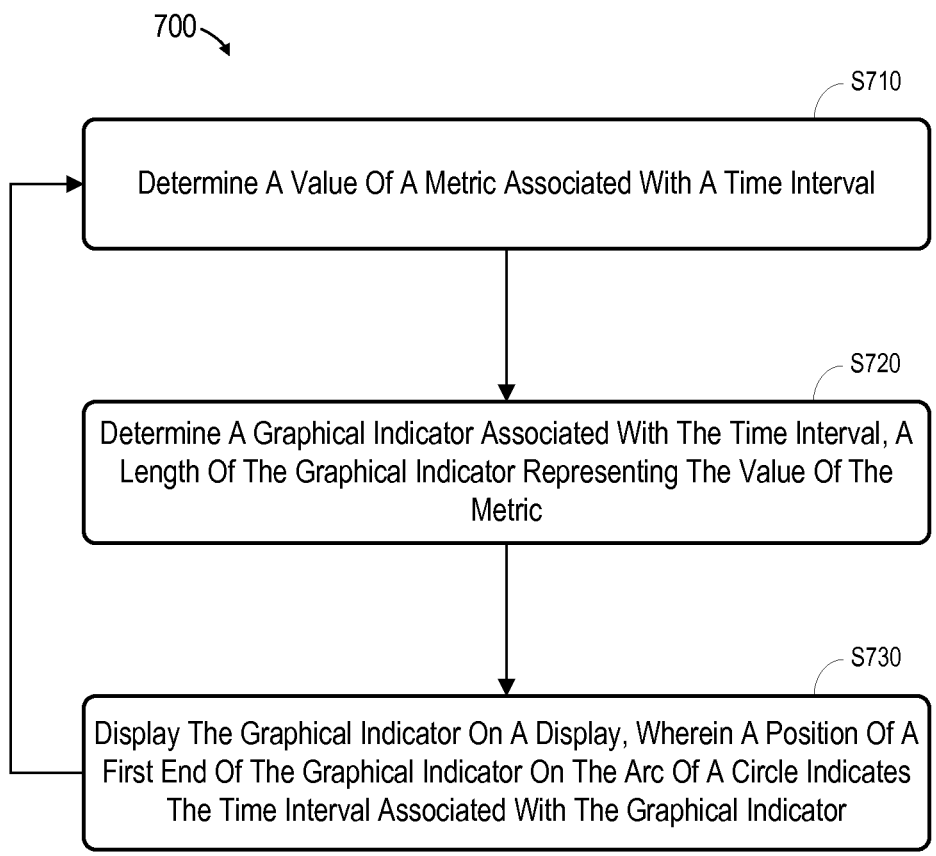
FIG. 7 is a flow diagram of a process according to some embodiments.

FIG. 7 is a flow diagram of process 700 according to some embodiments. Process 700 and the other processes described herein may be performed using any suitable combination of hardware or software, including implementations of system 300, device 400 and/or device 500. Software embodying these processes may be stored by any non-transitory tangible medium, including a fixed disk, a floppy disk, a CD, a DVD, a Flash drive, or a magnetic tape.

Initially, at S710, a value of a metric is determined for a particular time interval. The metric may comprise any metric described herein or that is (or becomes) known. The value of the metric may be indicative of physical activity, as also described above.

The value may be determined based on data/signals acquired from any number of sources. According to some embodiments, sensor 610 of device 500 acquires signals from contact with a user over a time interval and determines a value of a heart rate metric based on the detected signals. In some embodiments, an accelerometer of device 500 detects movement during a time interval and determines a step count value based on the detected movement. Determination of the value may also be based on stored data, such as user body characteristics, dietary information, etc.

Next, at S720, a graphical indicator associated with the time interval is determined. As described above, a length of the graphical indicator represents the determined value of the metric. The determined value may further be represented by colors, shapes or other graphical characteristics of the graphical indicator.

Figure 8:
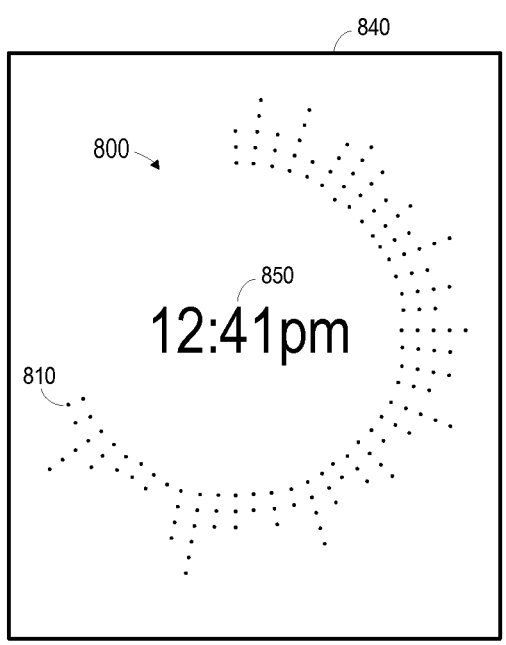
FIG. 8 is an outward view of displayed graphical indicators and a current time according to some embodiments.

The graphical indicator is displayed on a display at S730. A position of a first end of the graphical indicator on the arc of a circle indicates the time interval associated with the graphical indicator. FIG. 8 provides an example of the foregoing. It will be assumed that graphical indicator 810 is displayed on display 840 at S730. A first end of graphical indicator 810 and the other previously-displayed graphical indicators of visualization 800 substantially trace an arc of a circle. A position of the first end of graphical indicator 810 on the arc indicates the time interval associated with the graphical indicator 810. The indicated time interval, based on visualization 800's implied layout of an analog clock, is the fortieth minute of the current hour.

According to some embodiments, the angular distance of the arc traced by the graphical indicators indicates the current time. For example, if graphical indicator 810 is associated with the fortieth minute of the current hour, then the current time is forty-first minute of the current hour. Although the graphical indicators therefore provide an intuitive indication of the current time, visualization 800 also includes the current time 850 in the center of the circle which is implicitly formed by the graphical indicators.

Flow returns to S710 from S730 and continues as described above. Specifically, a second value of the metric is determined for a second time interval, a second graphical indicator associated with the second time interval is determined based on the second value of the metric, and the second graphical indicator is displayed such that a position of a first end of the second graphical indicator on the arc of a circle indicates the second time interval.

Figure 9:
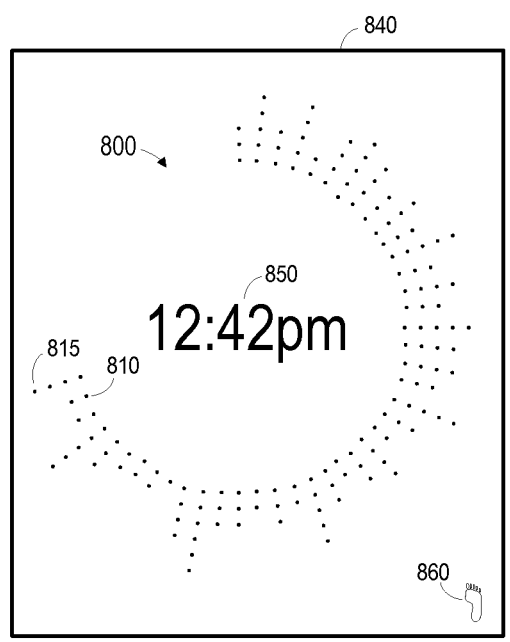
FIG. 9 is an outward view of displayed graphical indicators and a current time according to some embodiments.

FIG. 9 illustrates visualization 800 after a subsequent execution of S710-S730. Graphical indicator 815 is now displayed in display 840, along with new current time 850. A position of the first end of graphical indicator 815 on the arc indicates the forty-first minute of the current hour. Also, according to the embodiment of FIG. 9, visualization 800 also includes icon 860, which identifies the metric (i.e., step count) whose values are represented by the displayed graphical indicators.

Figure 10A:
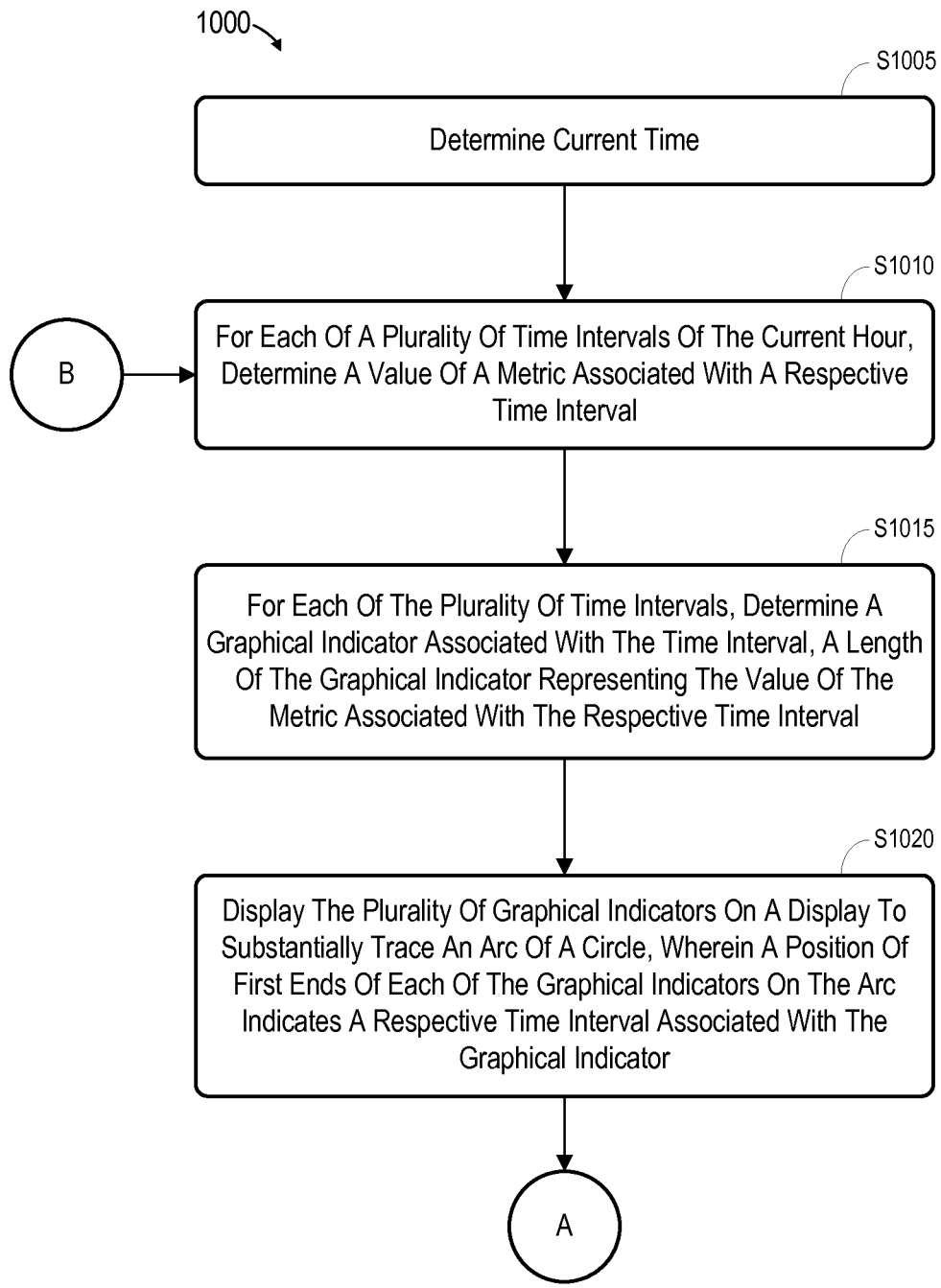
FIGS. 10A and 10B comprise a flow diagram of a process according to some embodiments.
Figure 10B:
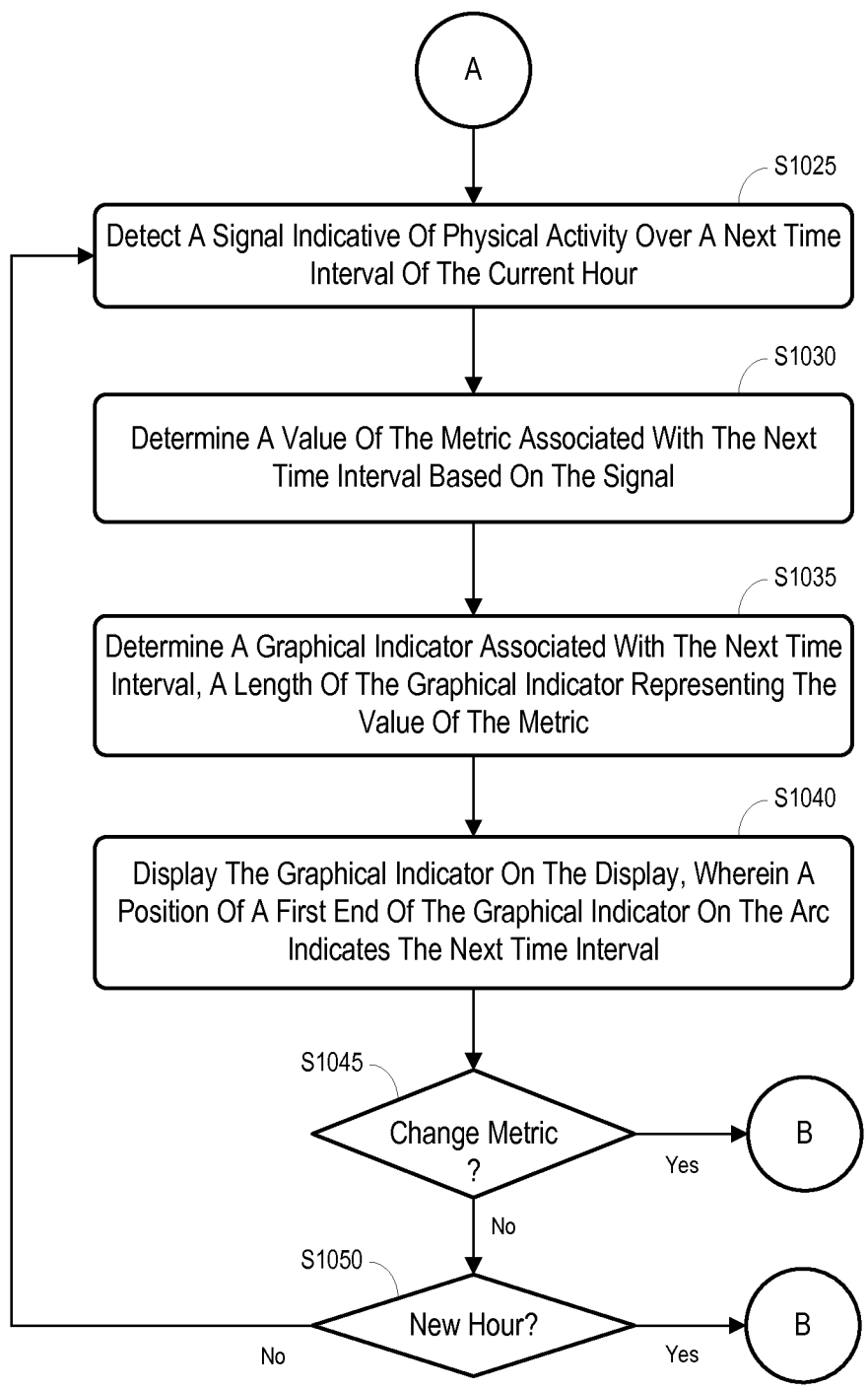

FIGS. 10A and 10B comprise process 1000 according to some embodiments. Embodiments are not, however, limited to the features of process 1000.

Prior to process 1000, it will be assumed that a device embodying process 1000 is activated (i.e., powered on, woken from sleep, etc.) or otherwise instructed to enter a mode for displaying a visualization according to some embodiments.

Initially, at S1005, a current time is determined. The current time may be determined from a network to which the device is connected (i.e., wired or wirelessly), from an on-board clock, or by other means.

Next, at S1010, a value of a metric is determined for each of a plurality of time intervals of the current hour. For example, it will be assumed that a current time of 12:41 pm is determined at S1005. According to some embodiments, a value of the metric is determined for each completed minute of the current hour (i.e., for each of forty completed minutes). Time intervals are not limited to single minutes in some implementations, as described above. It will be assumed that the metric in the current example is step count, therefore forty step count values are determined at S1010.

For each of the plurality of time intervals, a graphical indicator associated with the time interval is determined at S1015. As previously described, a length of a graphical indicator represents the value of the metric for the time interval associated with the graphical indicator. The plurality of graphical indicators are displayed at S1020 to substantially trace an arc of a circle. FIG. 8 provides an illustration of such a display according to the present example. As shown, a position of a first end of each of the plurality of graphical indicators on the arc indicates a time interval associated with each graphical indicator.

Next, at S1025, a signal indicative of physical activity over a next time interval is detected. In the present example, the next time interval is the forty-first minute of the hour, since values have been determined for the initial forty minutes of the hour. The signal may be detected by a sensor such as those already described. More than one signal from more than one sensor may be detected at S1025, depending on the information needed to determine a value of the particular metric being evaluated. In this regard, a next value of the metric is determined at S1030 and, as described with respect to S720, a graphical indicator representing the value and associated with the next time interval is determined at S1035.

As illustrated by graphical indicator 815 of FIG. 9, the graphical indicator determined at S1035 is displayed at S1040. A position of a first end of the graphical indicator on the arc indicates its associated time interval (i.e., the forty-first minute).

At S1045, it is then determined whether the metric of interest has changed. According to some embodiments, the metric of interest may change to another metric based on a schedule, in which case S1045 consists of confirming the schedule. In some embodiments, a user may issue a command to change the schedule. The command may be issued via buttons such as buttons 580, or by performing a touch screen gesture, such as a swipe, upon display 540. Any suitable input modality may be used to issue such a command.

If it is not determined to change the metric at S1045, it is determined whether the current time has entered a new hour. If not, flow continues to S1025 and to determine a new value and to display a corresponding new graphical indicator at an appropriate position on the arc of the circle.

Figure 11:
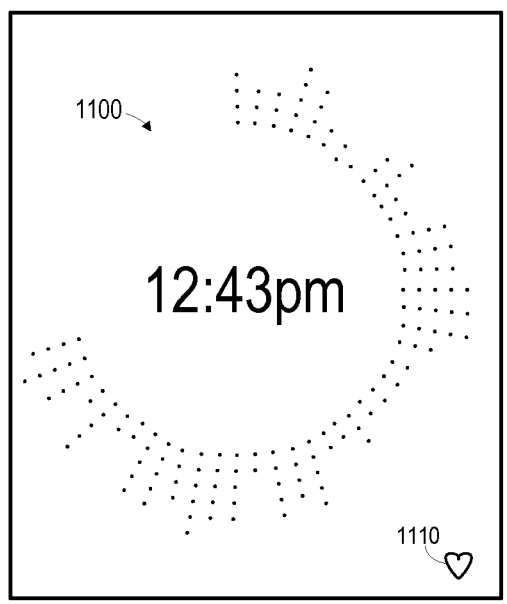
FIG. 11 is an outward view of displayed graphical indicators and a current time according to some embodiments.

Upon determining at S1045 that the metric is to be changed, flow returns to S1010 to determine a plurality of values of the new metric for a plurality of time intervals of the current hour (S1010), to determine a graphical indicator for each of the values (S1015), and to display the graphical indicators (S1020). FIG. 11 illustrates display of such graphical indicators according to some embodiments. Each graphical indicator of visualization 1100 represents a value of the new metric (e.g., heart rate) associated with a time interval indicated by a position of the graphical indicator. Icon 1110 now indicates the new metric, signaling to the user that the metric has changed.

Figure 12:
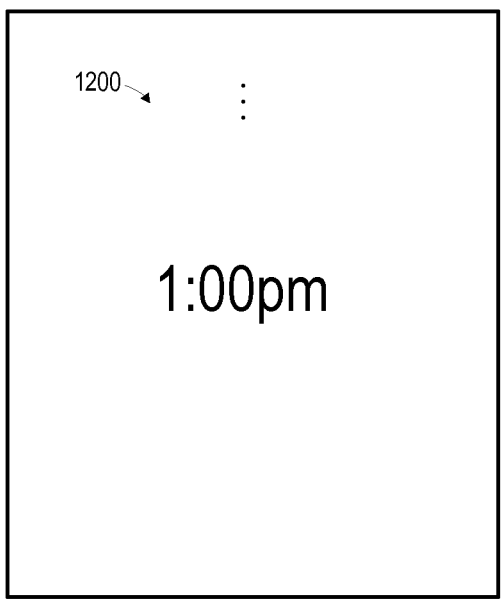
FIG. 12 is an outward view of displayed graphical indicators and a current time according to some embodiments.

On the other hand, if it is determined at S1050 that a new hour has arrived, flow returns to S1010 to determine a plurality of values of the new metric for a plurality of time intervals of the new hour (S1010), to determine a graphical indicator for each of the values (S1015), and to display the graphical indicators (S1020). Upon returning to S1010 from S1050 during the first minute of the hour, no time intervals of the new hour will have elapsed, so the first value and graphical indicator of the hour are determined at S1030 and S1035. The graphical indicator is displayed at S1040 as part of a new visualization, as illustrated by visualization 1200 of FIG. 12. Flow may then continue as described above to determine and display graphical indicators associated with the current metric or with another metric detected at S1045.

The foregoing diagrams represent logical architectures for describing processes according to some embodiments, and actual implementations may include more or different components arranged in other manners. Other topologies may be used in conjunction with other embodiments. Moreover, each system described herein may be implemented by any number of devices in communication via any number of other public and/or private networks. Two or more of such computing devices may be located remote from one another and may communicate with one another via any known manner of network(s) and/or a dedicated connection. Each device may include any number of hardware and/or software elements suitable to provide the functions described herein as well as any other functions. For example, any computing device used in an implementation of some embodiments may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Flash drive, magnetic tape, and solid state Random Access Memory (RAM) or Read Only Memory (ROM) storage units. Embodiments are therefore not limited to any specific combination of hardware and software.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A device, comprising:
   a display;
   a sensor to detect a signal indicative of physical activity;
   one or more processors;
   a memory; and
   program code, wherein the program code is stored in the memory and configured to be executed by the one or more processors, the program code including instructions for:

for each of a plurality of time intervals, determining a value of a metric associated with a respective time interval based on a signal indicative of physical activity detected by the sensor during the respective time interval; and displaying a plurality of graphical indicators on the display, each of the plurality of graphical indicators associated with a respective one of the plurality of time intervals, a characteristic of each displayed graphical indicator representing a value of a metric associated with the respective time interval of the displayed graphical indicator, wherein a first end of each of the plurality of displayed graphical indicators is located on an arc of a circle and disposed between a respective second end of the displayed graphical indicator and a center of the circle, the plurality of displayed graphical indicators substantially imply a layout of an analog clock and the circle represents an hour, and wherein, for each graphical indicator, a position of the first end of the graphical indicator with respect to the analog clock indicates the respective time interval within the hour associated with the graphical indicator.

2. A device according to claim 1,
wherein the value of the metric associated with a respective time interval is indicative of physical activity during the respective time interval.

3. A device according to claim 1, wherein the sensor comprises at least one of:
an accelerometer;
a light sensor;
a blood oxygen sensor;
a gyroscope;
a magnetometer;
a Global Positioning System device;
a proximity sensor,
an altimeter; and
a heart rate sensor.

4. A device according to claim 1, wherein the metric comprises one of: step count, heart rate, distance traveled, activity level, altitude changes, altitude ascended, altitude descended, floors climbed, and calories burned.

5. A device according to claim 1,
wherein the time intervals associated with each of the plurality of graphical indicators total one hour.

6. A device according to claim 1, the program code further including instructions for:
displaying a digital numerical representation of a current time along with the plurality of graphical indicators.

7. A device according to claim 1, the program code further including instructions for displaying along with the plurality of graphical indicators one of a current value of a step count, a current value of a heart rate, a current value of a distance traveled, a current value of an activity level, a current value of an altitude change, a current value of an altitude ascended, a current value of an altitude descended, a current value of floors climbed, and a current value of calories burned.

8. A device according to claim 1,
wherein an angular distance circumscribed by the plurality of graphical indicators indicates a current time.

9. A device according to claim 1,
wherein one of the plurality of graphical indicators associated with a respective time interval comprises M graphical icons, and
wherein M represents a value of the metric associated with the respective time interval.

10. A device according to claim 1, the program code further including instructions for:
determining that a next hour has begun;
ceasing display of at least some of the displayed graphical indicators associated with time intervals within the hour; and
displaying a graphical indicator associated with a first time interval of the next hour.

11. A device, comprising:
a display;
a sensor to detect a signal indicative of physical activity;
one or more processors;
a memory; and
program code, wherein the program code is stored in the memory and configured to be executed by the one or more processors, the program code including instructions for:
for each of a plurality of time intervals, determining a value of a metric associated with a respective time interval based on a signal indicative of physical activity detected by the sensor during the respective time interval; and
displaying a plurality of graphical indicators on the display, each of the plurality of graphical indicators comprising a respective number of graphical icons and associated with a respective one of the plurality of time intervals, and the respective number of graphical icons of each displayed graphical indicator representing a value of a metric associated with the respective time interval of the displayed graphical indicator, the value of the metric being indicative of physical activity during the respective time interval, wherein a first ends of each of the plurality of displayed graphical indicators is located on an arc of a circle and disposed between a respective second end of the displayed graphical indicator and a center of the circle, the plurality of displayed graphical indicators substantially imply a layout of an analog clock and the circle represents an hour, and wherein, for each graphical indicator, a position of the first end of the graphical indicator with respect to the analog clock indicates the respective time interval within the hour associated with the graphical indicator.

12. A device according to claim 11,
wherein an angular distance circumscribed by the plurality of graphical indicators indicates a current time.

13. A device according to claim 11, wherein the sensor comprises at least one of:
an accelerometer;
a light sensor;
a blood oxygen sensor;
a gyroscope;
a magnetometer;
a Global Positioning System device;
a proximity sensor,
an altimeter; and
a heart rate sensor.

14. A device according to claim 11, wherein the metric comprises one of: step count, heart rate, distance traveled, activity level, altitude changes, altitude ascended, altitude descended, floors climbed, and calories burned.

15. A device according to claim 11,
wherein the time intervals associated with each of the plurality of graphical indicators total one hour.

16. A device according to claim 11, the program code further including instructions for displaying along with the plurality of graphical indicators one of a current value of a step count, a current value of a heart rate, a current value of a distance traveled, a current value of an activity level, a current value of an altitude change, a current value of an altitude ascended, a current value of an altitude descended, a current value of floors climbed, and a current value of calories burned.

17. A device according to claim 11,
wherein one of the plurality of graphical indicators associated with a respective time interval comprises M graphical icons, and
wherein M represents a value of the metric associated with the respective time interval.

18. A device according to claim 17,
wherein each graphical icon represents N units of the metric, and the value of the metric is approximately equal to M*N.

19. A device according to claim 11,
wherein a digital numerical representation of a current time is displayed along with the plurality of graphical indicators.

20. A device according to claim 11, the program code further including instructions for:
determining that a next hour has begun;
ceasing display of at least some of the displayed graphical indicators associated with time intervals within the hour; and
displaying a graphical indicator associated with a first time interval of the next hour.

21. A method, comprising:
detecting, using a sensor, a signal indicative of physical activity;
for each of a plurality of time intervals, determining a value of a metric associated with a respective time interval based on a signal indicative of physical activity detected by the sensor during the respective time interval; and
displaying a plurality of graphical indicators on a display, each of the plurality of graphical indicators associated with a respective one of the plurality of time intervals, and, a characteristic of each displayed graphical indicator representing a value of a metric associated with the respective time interval of the displayed graphical indicator,
wherein a first ends of each of the plurality of displayed graphical indicators is located on an arc of a circle and disposed between a respective second end of the displayed graphical indicator and a center of the circle, the plurality of displayed graphical indicators substantially imply a layout of an analog clock and the circle represents an hour, and
wherein, for each graphical indicator, a position of the first end of the graphical indicator with respect to the analog clock indicates the respective time interval within the hour associated with the graphical indicator.

22. A method according to claim 21, further comprising:
displaying a digital numerical representation of a current time along with the plurality of graphical indicators,
wherein an angular distance circumscribed by the plurality of graphical indicators represents the current time.

23. A method according to claim 21,
wherein one of the plurality of graphical indicators associated with a respective time interval comprises M graphical icons, and
wherein M represents a value of the metric associated with the respective time interval.

24. A method according to claim 21, further comprising:
displaying a digital numerical representation of a current time along with the plurality of graphical indicators.

25. A method according to claim 21, comprising:
determining that a next hour has begun;
ceasing display of at least some of the displayed graphical indicators associated with time intervals within the hour; and
displaying a graphical indicator associated with a first time interval of the next hour.

26. A method, comprising:
detecting, using a sensor, a signal indicative of physical activity;
for each of a plurality of time intervals, determining a value of a metric associated with a respective time interval based on a signal indicative of physical activity detected by the sensor during the respective time interval; and
displaying a plurality of graphical indicators on a display, each of the plurality of graphical indicators comprising a respective number of graphical icons and associated with a respective one of the plurality of time intervals, and the respective number of graphical icons of each graphical indicator representing a value of a metric associated with the respective time interval of the displayed graphical indicator, the value of the metric being indicative of physical activity during the respective time interval,
wherein a first ends of each of the plurality of displayed graphical indicators is located on an arc of a circle and disposed between a respective second end of the displayed graphical indicator and a center of the circle, the plurality of displayed graphical indicators substantially imply a layout of an analog clock and the circle represents an hour, and
wherein, for each graphical indicator, a position of the first end of the graphical indicator with respect to the analog clock indicates the respective time interval within the hour associated with the graphical indicator.

27. A method according to claim 26, further comprising
displaying a digital numerical representation of a current time along with the plurality of graphical indicators,
wherein an angular distance circumscribed by the plurality of graphical indicators represents the current time.

28. A method according to claim 26, further comprising:
displaying a digital numerical representation of a current time along with the plurality of graphical indicators.

29. A method according to claim 26, comprising:
determining that a next hour has begun;
ceasing display of at least some of the displayed graphical indicators associated with time intervals within the hour; and
displaying a graphical indicator associated with a first time interval of the next hour.

* * * * *